(12) United States Patent
Saukaitis et al.

(10) Patent No.: US 10,272,381 B2
(45) Date of Patent: Apr. 30, 2019

(54) METHOD USING CARBON MONOXIDE RESISTANT MEMBRANE TO CONTROL H2/CO RATIO OF SYNTHESIS GAS FEED TO FISCHER-TROPSCH UNIT

(71) Applicant: SHELL OIL COMPANY, Houston, TX (US)

(72) Inventors: John Charles Saukaitis, Katy, TX (US); Kamal Azad, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/558,720

(22) PCT Filed: Mar. 16, 2016

(86) PCT No.: PCT/US2016/022555
§ 371 (c)(1),
(2) Date: Sep. 15, 2017

(87) PCT Pub. No.: WO2016/149310
PCT Pub. Date: Sep. 22, 2016

(65) Prior Publication Data
US 2018/0065080 A1    Mar. 8, 2018

Related U.S. Application Data

(60) Provisional application No. 62/134,642, filed on Mar. 18, 2015.

(51) Int. Cl.
*B01D 53/22* (2006.01)
*C01B 3/50* (2006.01)
(Continued)

(52) U.S. Cl.
CPC ........ *B01D 53/228* (2013.01); *B01D 71/022* (2013.01); *C01B 3/505* (2013.01);
(Continued)

(58) Field of Classification Search
CPC .............................................. C10G 2300/1011
See application file for complete search history.

(56) References Cited

U.S. PATENT DOCUMENTS 8,721,773 B2    5/2014    Perkins, II et al.
2004/0102532 A1    5/2004    Landis et al.
(Continued)

OTHER PUBLICATIONS

International Search Report and Written Opinion received for PCT Patent Application No. PCT/US2016/22555, dated Jun. 13, 2016, 6 pages.

*Primary Examiner* — Medhanit W Bahta
(74) *Attorney, Agent, or Firm* — Charles W. Stewart

(57) ABSTRACT

An integrated process for making high molecular weight hydrocarbons from a synthesis gas feed to a Fischer-Tropsch unit. A carbon monoxide resistant gold-on-palladium membrane system (membrane system) is used to control the hydrogen-to-carbon monoxide molar ratio of a feed to the Fischer-Tropsch unit. The membrane system is operatively connected between a steam reformer and the Fischer-Tropsch unit. The membrane system receives a synthesis gas stream and provides for the removal of hydrogen from the synthesis gas stream to provide a retentate stream having a desired $H_2/CO$ molar ratio that is fed to the Fischer-Tropsch unit.

12 Claims, 2 Drawing Sheets

(51) Int. Cl.
*C10G 2/00* (2006.01)
*B01D 71/02* (2006.01)
*C07C 1/04* (2006.01)

(52) U.S. Cl.
CPC .................. *C07C 1/04* (2013.01); *C10G 2/32* (2013.01); *B01D 2256/16* (2013.01); *B01D 2256/20* (2013.01); *B01D 2257/108* (2013.01); *C01B 2203/0233* (2013.01); *C01B 2203/0405* (2013.01); *C01B 2203/062* (2013.01); *C01B 2203/1058* (2013.01); *C01B 2203/1064* (2013.01); *C01B 2203/1241* (2013.01); *Y02P 20/125* (2015.11)

(56) References Cited

U.S. PATENT DOCUMENTS

| | | | |
|---|---|---|---|
| 2009/0165385 A1 | 7/2009 | You et al. | |
| 2012/0138316 A1* | 6/2012 | Matzakos | C09K 8/592 166/400 |
| 2012/0325087 A1 | 12/2012 | Tsai et al. | |
| 2014/0047763 A1* | 2/2014 | Chakravarti | C01B 3/36 44/457 |
| 2014/0251131 A1* | 9/2014 | Way | B01D 71/022 95/56 |
| 2015/0290591 A1 | 10/2015 | Saukaitis et al. | |
| 2015/0292090 A1 | 10/2015 | Saukaitis et al. | |

* cited by examiner

METHOD USING CARBON MONOXIDE RESISTANT MEMBRANE TO CONTROL H2/CO RATIO OF SYNTHESIS GAS FEED TO FISCHER-TROPSCH UNIT

PRIORITY CLAIM

The present application is the National Stage (§ 371) of International Application No. PCT/US2016/022555, filed Mar. 16, 2016, which claims priority from U.S. Patent Application No. 62/134,642, filed Mar. 18, 2015 incorporated herein by reference.

This invention relates to an integrated process for making high molecular weight hydrocarbons from synthesis gas feed to a Fischer-Tropsch synthesis step in which the $H_2/CO$ ratio of the synthesis gas feed is controlled using a carbon monoxide resistant gold-on-palladium gas separation membrane system.

BACKGROUND OF THE INVENTION

The Fischer-Tropsch process provides for the processing of synthesis gas, which comprises hydrogen and carbon monoxide, to yield high molecular weight hydrocarbons. Steam reforming is one process that provides for the processing of desulfurized hydrocarbon feedstocks, such as natural gas, lower molecular weight hydrocarbons, or naphtha, to yield synthesis gas that may be used as a feed to a Fischer-Tropsch synthesis process.

In the steam reforming process, the desulfurized hydrocarbon feedstock is mixed with steam and passed over a suitable catalyst, e.g., a catalyst comprising nickel on an alumina support, at an elevated temperature and pressure to yield a synthesis gas. The synthesis gas comprises hydrogen and carbon monoxide at concentrations providing for particular hydrogen-to-carbon monoxide molar ratios ($H_2/CO$ ratio).

In the Fischer-Tropsch process, the synthesis gas is fed into a reactor where it is converted over a suitable catalyst, e.g., cobalt or iron, preferably, cobalt, supported on alumina, silica, or titania, at elevated temperature and pressure into paraffinic compounds ranging from methane to high molecular weight molecules comprising up to or more than 200 carbon atoms. The product distribution of the Fischer-Tropsch synthesis is influenced by the $H_2/CO$ ratio of the synthesis gas feed due to typical selectivity characteristics of the Fischer-Tropsch catalysts. Reactions with lower $H_2/CO$ ratios are more selective for yielding C5+ hydrocarbon molecules, and reactions with higher $H_2/CO$ ratios are less selective for yielding C5+ hydrocarbon molecules.

In a process that integrates a reforming step that yields a synthesis gas with a Fischer-Tropsch synthesis step that reacts the synthesis gas to yield high molecular weight hydrocarbons, it can be desirable to control the $H_2/CO$ ratio of the synthesis gas feed to the Fischer-Tropsch synthesis step. By controlling the $H_2/CO$ ratio of Fischer-Tropsch feed, the Fischer-Tropsch product properties can, to a certain extent, be controlled to provide a desired Fischer-Tropsch product mix.

Thus, it is desirable to have a process that includes a unit for reforming hydrocarbon feeds and a means for controlling the $H_2/CO$ ratio of the synthesis gas feed to a Fischer-Tropsch unit.

BRIEF SUMMARY OF THE INVENTION

Accordingly, provided is a process for converting gaseous hydrocarbons to higher molecular weight hydrocarbons. The process comprises providing a carbon monoxide resistant gold-on-palladium supported gas separation membrane system that is operatively connected between a steam reforming unit and a Fischer-Tropsch unit. At least a portion of a synthesis gas stream yielded from the steam reforming unit and having a synthesis gas stream hydrogen-to-carbon monoxide ratio is passed as a membrane system feed to the carbon monoxide resistant gold-on-palladium supported gas separation membrane system. A permeate stream, comprising hydrogen, and a retentate stream, having a retentate stream hydrogen-to-carbon monoxide ratio are yielded from the carbon monoxide resistant gold-on-palladium supported gas separation membrane system. The retentate stream is passed as a Fischer-Tropsch unit feed to the Fischer-Tropsch unit, and a synthesis product is yielded from the Fischer-Tropsch unit.

DETAILED DESCRIPTION OF THE INVENTION

Figure 1:
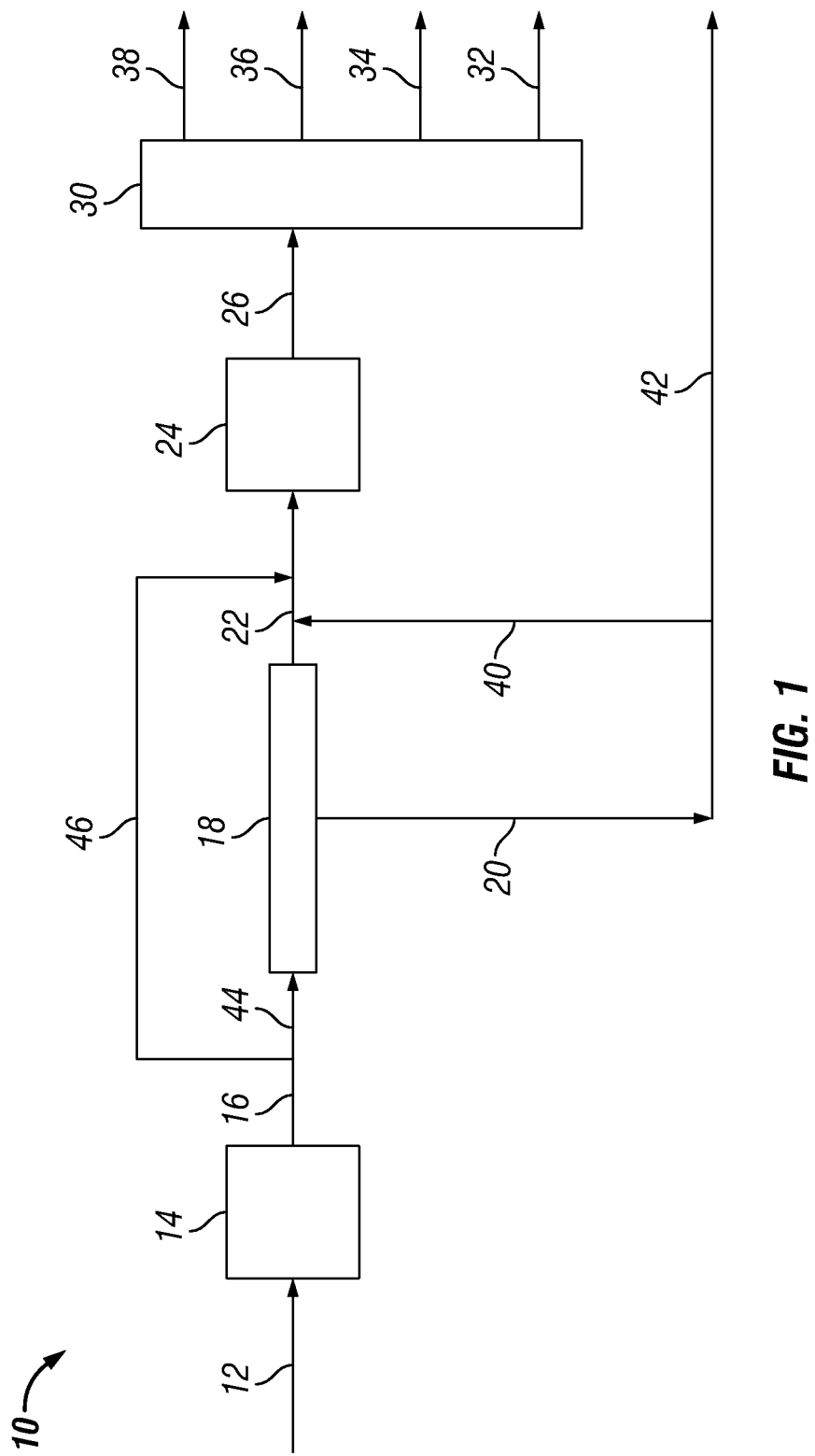
FIG. 1 is a process flow diagram of the inventive process that utilizes a carbon monoxide resistant gold-on-palladium membrane system integrated with a steam reforming unit and a Fischer-Tropsch unit to make high molecular weight hydrocarbons from a synthesis gas derived feed.

In the Fischer-Tropsch process, synthesis gas, comprising hydrogen and carbon monoxide, is reacted over a Fischer-Tropsch catalyst, under suitable reaction conditions, to yield a range of hydrocarbons that preferably have five or more carbon atoms per hydrocarbon molecule. The following is the representative Fischer-Tropsch reaction equation:

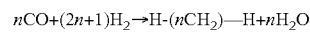

$$nCO + (2n+1)H_2 \rightarrow H\text{-}(nCH_2)\text{---}H + nH_2O$$

It is generally preferred for the Fischer-Tropsch reaction product to comprise predominantly liquid hydrocarbons, and, among these, it is most preferred for the reaction product to comprise hydrocarbons having five or more carbon atoms per molecule. Yielding of hydrocarbons having boiling temperatures in the gasoline, kerosene, diesel, gas oil and heavier boiling ranges is preferred. High yields of waxy hydrocarbons are often especially preferred.

It is recognized that the composition of the Fischer-Tropsch reaction product is influenced by the hydrogen-to-carbon monoxide ratio ($H_2/CO$ ratio) of the synthesis gas feed to the Fischer-Tropsch unit. Generally, lower ratios of $H_2/CO$ promote the production of heavier hydrocarbon products and higher ratios of $H_2/CO$ tend to cause the production of lighter hydrocarbon products. Due to this relationship, the Fischer-Tropsch reaction product composition can, to a certain extent, be influenced or controlled by modifying or adjusting the $H_2$/CO ratio of the synthesis gas feed so as to provide for a desired Fischer-Tropsch reaction product composition.

One problem that is encountered with the integration of a steam reforming unit with a Fischer-Tropsch unit is that the $H_2$/CO ratio of the yielded synthesis gas stream from the steam reforming unit charged to the Fischer-Tropsch unit can be unacceptably high such that the Fischer-Tropsch reaction product fails to comprise the desired profile of heavier hydrocarbons. The inventive process solves this problem by providing a noble metal gas separation membrane system that is operatively connected between the steam reforming unit and the Fischer-Tropsch unit so as to provide for the separation of hydrogen from the synthesis gas stream to raise the $H_2$/CO ratio of the Fischer-Tropsch unit feed.

Various other types of membranes, such as polymeric membranes, have been proposed for use in separating hydrogen from a synthesis gas stream. But, most are unsuitable for the application; because, they cannot be used at the desired high temperatures or high pressures, or both, and they have unacceptably low selectivity and permeability.

Certain noble metal membranes have also been proposed for use in separating hydrogen from synthesis gas; because, they can tolerate operating at reasonably high temperatures and pressures, and they tend to be more selective and permeant at the higher temperatures and pressures than alternative membranes.

It unexpectedly has been discovered, however, that the performance of palladium-only membranes when used in the separation of hydrogen from gas streams that also include carbon monoxide is unstable in the presence of relatively low concentrations of the carbon monoxide. The separation efficiency of the palladium-only membrane tends to rapidly decline when the concentration of carbon monoxide of the process gas reaches levels of greater than 7.5 volume percent. This performance loss characteristic makes the use of palladium-only membranes for the separation of hydrogen from synthesis gas streams impractical due to the high carbon monoxide concentration of the synthesis gas.

It is further unexpected that, unlike the palladium-only membranes, the hydrogen separation performance of gold-on-palladium gas separation membranes, such as those disclosed in U.S. Pat. No. 8,721,773, issued May 13, 2014, and the references cited therein, is stable in the presence of significant concentration levels of carbon monoxide. This carbon monoxide resistance characteristic of the gold-on-palladium gas separation membranes to the performance decline caused by high concentrations of carbon monoxide make their use advantageous in the separation of hydrogen from synthesis gas due to its high concentration of carbon monoxide.

Thus, an important aspect of the inventive process is the application and use of the carbon monoxide resistant gold-on-palladium gas separation membrane system, which includes a gold-on-palladium membrane, in an integrated process for converting gaseous hydrocarbons to higher molecular weight hydrocarbons. The integrated process includes a steam reforming unit that yields a synthesis gas and a Fischer-Tropsch unit that receives a Fischer-Tropsch unit feed that is derived from the synthesis gas for conversion into a Fischer-Tropsch synthesis product. The carbon monoxide resistant gold-on-palladium gas separation membrane system that includes a gold-on-palladium membrane is operatively connected between the steam reforming unit so as to receive as a membrane system feed the synthesis gas and the Fischer-Tropsch unit, which receives as a Fischer-Tropsch unit feed the retentate discharged from the carbon monoxide resistant gold-on-palladium gas separation membrane system.

The synthesis gas stream that is passed as a membrane system feed to the carbon monoxide resistant gold-on-palladium supported gas separation membrane system is provided by any suitable process or system for making a synthesis gas stream, comprising hydrogen and carbon monoxide, and having a synthesis gas stream hydrogen-to-carbon monoxide ratio. Steam reforming of hydrocarbons is one process that is known to those skilled in the art for making synthesis gas.

The steam reforming unit of the inventive process yields a synthesis gas stream of which at least a portion is passed to the carbon monoxide resistant gold-on-palladium supported gas separation membrane system as a membrane system feed. The steam reforming process comprises contacting a mixture of a hydrocarbon feedstock and steam with a reforming catalyst under suitable steam reforming conditions to yield the synthesis gas stream. The following is the representative steam reforming equilibrium reaction equation for reforming methane:

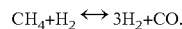

$$CH_4 + H_2 \leftrightarrow 3H_2 + CO.$$

The hydrocarbon feedstock to the steam reforming unit can be natural gas (methane), low molecular weight hydrocarbons, such as ethane, propane, and butane, and even naphtha. The preferred hydrocarbon feedstock to the steam reforming unit is methane or natural gas. Steam is mixed with the hydrocarbon feedstock to provide the reformer feed mixture that is contacted with the reformer catalyst. The amount of steam used is such as to provide a steam-to-hydrocarbon molar ratio of the reformer feed mixture in the range of from 0.5:1 to 2:1. It is preferred to limit the excess amount of steam of the reforming reaction. Thus, the steam-to-hydrocarbon molar ratio is preferably less than 1.5:1, and, more preferably, less than 1.25:1. The steam-to-hydrocarbon molar ratio can, therefore, be in the range of from 0.5:1 to 1.5:1, or from 0.5:1 to 1.25:1.

The reforming catalyst used in the steam reforming unit may be any catalyst known to those skilled in the art and that suitably provides for the reforming of the hydrocarbons to yield an appropriate synthesis gas for use as the membrane system feed of the inventive process. Generally, the reforming catalyst includes a catalytically active metal supported on a suitable refractory support. The refractory support may be a shape, such as a ring, or an extrudate, or a ball, or any other shape, that comprises the refractory material, such as alumina or calcium aluminate cement, titania, zirconia, or refractory materials. Nickel can be a suitable catalytic metal for the reforming catalyst, but the precious metals of rhodium, ruthenium and platinum may also be used either alone or in combination with other metals such as nickel.

The reforming reaction conditions can include a steam reforming reaction temperature in the range of from 600 to 950° C. and a steam reforming reaction pressure in the range of from 25 atm to 100 atm.

The synthesis gas stream that is yielded from the steam reforming unit comprises hydrogen and carbon monoxide. It can also comprise significant concentrations of steam and at least one hydrocarbon, such as methane, because steam and hydrocarbon are reactants of the steam reforming reaction.

Typically, the synthesis gas stream comprises hydrogen in an amount in the range of from 30 to 70 vol. %. More typically, the concentration of hydrogen in the synthesis gas stream is in the range of from 40 to 60 vol. %, and, more typically, it is from 45 to 55 vol. %. The amount of methane in the synthesis gas stream can be in the range of from 1 to 10 vol. %, or in the range of from 2 to 8 vol. %, or from 4 to 6 vol. %.

The relative amounts of hydrogen and carbon monoxide in the synthesis gas stream are such that the hydrogen-to-carbon monoxide ($H_2/CO$) molar ratio in the synthesis gas stream is in the range of from 1.5:1 to 10:1. More typically, however, the $H_2/CO$ molar ratio is in the range of from 1.6:1 to 4:1. It is desirable for the $H_2/CO$ molar ratio to be in the range of from 1.7:1 to 3:1, and, more desirably, it is in the range of from 1.8:1 to 2.5:1.

In systems that are integrated with a Fischer-Tropsch unit, sometimes the $H_2/CO$ molar ratio of the synthesis gas stream to be charged to the Fischer-Tropsch unit is undesirably high which can provide for a less favorable Fischer-Tropsch synthesis product composition.

The carbon monoxide resistant gold-on-palladium supported separation membrane system is integrated into the process system of the invention such that it is used in the control of the $H_2/CO$ molar ratio of the feed to the Fischer-Tropsch unit to provide for an improved or optimized Fischer-Tropsch synthesis product mix. This helps to address the problem associated with introducing high $H_2/CO$ molar ratio feeds to the Fischer-Tropsch unit.

The gold-on-palladium supported separation membrane system comprises a porous support, which is typically a tubular shape, having deposited on its surface a membrane layer of palladium on top of which is deposited a membrane overlayer of gold to provide a gas separation membrane system comprising a membrane comprising a gold layer on a palladium layer. The gold-on-palladium supported separation membrane system includes inlet means for receiving a membrane system feed, outlet means for discharging a retentate stream, and removing means for removing from the membrane system a permeate stream, comprising hydrogen.

More specifically defined gold-on-palladium supported separation membrane systems that suitably can be used in the inventive system and process include those described in U.S. Pat. No. 8,721,773 and those made by the methods described in U.S. Pat. No. 8,721,773, which patent is incorporated herein by reference.

The synthesis gas stream is introduced into the carbon monoxide resistant gold-on-palladium supported gas separation membrane system from which a permeate stream, comprising hydrogen, and a retentate stream, having a retentate stream $H_2/CO$ molar ratio that is less than the $H_2/CO$ molar ratio of the synthesis gas stream.

The carbon monoxide resistant gold-on-palladium supported gas separation membrane system operates at a temperature in the range of from 300 to 500° C. Preferably, the operating temperature is in the range of from 325 to 450° C., and, more preferably, from 350 to 400° C. The operating pressure of the membrane system is in the range of from 10 to 100 bar. Preferably, the operating pressure is in the range of from 7 to 70 bar, and, more preferably, from 10 to 50 bar.

It is a significant feature of the membrane system that it is able to operate at the high temperatures and pressures that are noted above. The ability to operate under these conditions provide for greater membrane permeance.

The concentration of hydrogen in the permeate stream should be greater than 95 vol. %, and, preferably, greater than 97 vol. %. More preferably, the hydrogen concentration of the permeate stream is greater than 98 vol. %.

In the typical operation of the inventive process or system, the permeate stream can comprise from 1 vol. % to 20 vol. % of the total hydrogen contained in the synthesis gas stream that is introduced into the membrane system. It is a generally desirable aspect of the inventive process for the permeate stream to comprise from 3 vol. % to 12 vol. % of the hydrogen contained in the synthesis gas stream that is introduced into the membrane system, and, preferably, the amount of hydrogen removed from the synthesis gas stream is in the range of from 3 vol. % to 12 vol. %. The removal of hydrogen from the synthesis gas stream allows for providing a retentate steam having a $H_2/CO$ molar ratio in the range of from 1.4:1 to 2.3:1, and, preferably, from 1.5:1 to 2.2:1.

As discussed above, the Fischer-Tropsch process is known in the art and provides for the reaction of carbon monoxide with hydrogen to form hydrocarbons that preferably have five or more carbon atoms per molecule. The synthesis product yielded from Fischer-Tropsch unit of the inventive process or system should, thus, comprise an amount of C5+ hydrocarbons of at least 60 wt. % of the synthesis product, and preferably, at least 70 wt. % of the synthesis product. Most preferably, the Fischer-Tropsch synthesis product comprises at least 85 wt. % synthesis product. The CO conversion is preferably at least 50 wt. % of the CO contained in Fischer-Tropsch unit feed.

The Fischer-Tropsch catalyst used in the Fischer-Tropsch unit may be any catalyst known to those skilled in art and that provides for the Fischer-Tropsch reaction to yield its synthesis product. Typically, the Fischer-Tropsch catalyst comprises a Group VIII metal component, preferably either cobalt, or iron, or ruthenium, or a combination thereof. Cobalt is a particularly preferred catalyst. The metal is usually supported by a porous carrier, such as a porous inorganic refractory oxide that is preferably selected from the group consisting of alumina, silica, titania, zirconia or combinations thereof.

In addition to the catalytically active metal present in the Fischer-Tropsch catalyst, it can also include one or more promoters or co-catalysts. The promoter metal may be present as a metal or as a metal oxide. Examples of possible suitable promoter metals include titanium, zirconium, manganese and/or vanadium.

The retentate stream of the inventive process is passed as a Fischer-Tropsch unit feed to the Fischer-Tropsch unit wherein it is contacted with a Fischer-Tropsch catalyst under suitable synthesis reaction conditions to yield a Fischer-Tropsch synthesis product. The Fischer-Tropsch reaction temperature is generally in the range of from 150 to 500° C., preferably, from 175 to 450° C., and, more preferably, from 200 to 400° C. The Fischer-Tropsch reaction pressure is generally in the range of from 1.4 MPa to 4.1 MPa, and, preferably, from 2 MPa to 3.5 MPa. The space velocity can be in the range of from 50 $hr^{-1}$ to 500 $hr^{-1}$, preferably, from 150 $hr^{-1}$ to 350 $hr^{-1}$.

There are several different embodiments of the invention that provide for the fine control of the $H_2/CO$ molar ratio of the Fischer-Tropsch unit feed to a desired $H_2/CO$ molar ratio. One of these embodiments includes controlling the pressure differential across the gold-on-palladium membrane so as to provide a retentate stream having a desired $H_2/CO$ molar ratio for feeding to the Fischer-Tropsch unit. The amount of hydrogen separation from the synthesis gas stream is influenced by the pressure differential across the separation membrane, thus, allowing for adjustments in the $H_2/CO$ molar ratio of the retentate stream by adjusting the pressure differential. A higher pressure differential will tend to lower the $H_2/CO$ molar ratio of the retentate and a lower pressure differential will tend to increase the $H_2/CO$ molar ratio retentate.

The desired $H_2/CO$ molar ratio can depend upon the particular Fischer-Tropsch synthesis product mix that is wanted, but, typically, is less than 2.1:1 and greater than 1.4:1. The desired $H_2/CO$ molar ratio can also be in the range of from 1.6:1 to 2:1.

In another embodiment of the inventive process that provides for the fine control of the desired $H_2/CO$ molar ratio of the Fischer-Tropsch unit feed includes combining a portion of the permeate stream with the retentate steam in an amount so as to provide the desired $H_2/CO$ molar ratio. The permeate stream is mostly hydrogen. Any addition of the permeate stream with the retentate stream will cause an increase in the resulting $H_2/CO$ molar ratio. Thus, if the $H_2/CO$ molar ratio of the retentate stream is lower than desired, a portion of the permeate stream can be mixed with the retentate stream in an amount so as to provide a desired $H_2/CO$ molar ratio for the feed to the Fischer-Tropsch unit.

A yet another embodiment of the inventive process that provides for the fine control of the desired $H_2/CO$ molar ratio of the Fischer-Tropsch unit feed includes feeding only a portion of the synthesis gas stream yielded from the steam reforming unit and combining the remaining portion of the synthesis gas stream with the retentate stream in amount so as to provide the desired $H_2/CO$ molar ratio of the feed to the Fischer-Tropsch unit. Because the $H_2/CO$ molar ratio of the synthesis gas stream is greater than that of the retentate stream, the addition of the remaining portion of the synthesis gas stream with the retentate stream will cause an increase in its $H_2/CO$ molar ratio.

Presented in FIG. 1 is a process flow diagram representative of the inventive integrated process 10 for making high molecular weight hydrocarbons from synthesis gas feed.

In process 10, a mixture of a hydrocarbon feedstock that typically comprises one or more low molecular weight gaseous hydrocarbons, such as methane, and steam passes by way of conduit 12 and is introduced into steam reforming unit 14.

In steam reforming unit 14 the mixture is contacted with a steam reforming catalyst under suitable reforming conditions to yield a synthesis gas. The synthesis gas comprises hydrogen ($H_2$) and carbon monoxide (CO). A synthesis gas stream passes from steam reforming unit 14 through conduit 16 and is introduced into carbon monoxide resistant gold-on-palladium supported gas separation membrane system (membrane system) 18. The synthesis gas stream has a particular synthesis gas $H_2/CO$ molar ratio.

The membrane system 18 provides for the separation of hydrogen from the synthesis gas to yield a permeate stream that comprises predominantly hydrogen, usually at a concentration of greater than 98 vol. %, and a retentate stream, having a retentate stream $H_2/CO$ molar ratio that is less than the $H_2/CO$ molar ratio of the synthesis gas stream. The permeate stream passes from membrane system 18 through conduit 20. The retentate stream passes from membrane system 18 by way of conduit 22 to be introduced as a Fischer-Tropsch feed to Fischer-Tropsch unit 24.

In Fischer-Tropsch unit 24 the retentate stream is contacted with a Fischer-Tropsch catalyst under suitable synthesis reaction conditions to yield a Fischer-Tropsch synthesis product, which comprises a mixture of liquid hydrocarbons, typically having 5 or more carbons per molecule, and preferably waxy hydrocarbons.

The Fischer-Tropsch synthesis product passes from Fischer-Tropsch unit 24 by way of conduit 26 and is introduced into separation system 30. Separation system 30 provides means for separating or further processing of portions of the Fischer-Tropsch synthesis product into various hydrocarbon components of various boiling ranges, such as the waxes (C19+), diesel (C12-C18), gasoline (C5-C11), and lighter hydrocarbons. The wax passes from separation system 30 by way of conduit 32. The diesel passes from separation system 30 by way of conduit 34. The gasoline passes from separation system 30 by way of conduit 36. The light hydrocarbons pass from separation system 30 by way of conduit 38.

In an embodiment of process 10, the $H_2/CO$ molar ratio of the feed to Fischer-Tropsch unit 24 is controlled by passing portion of the permeate stream to be mixed with the retentate stream. In this embodiment, a portion of the permeate stream passing through conduit 20 passes by way of conduit and is mixed with the retentate stream that is passing through conduit 22. The amount of permeate stream that is mixed with the retentate stream is such as to provide a feed to Fischer-Tropsch unit 24 having a desired $H_2/CO$ molar ratio. The remaining portion of the permeate stream passing through conduit 20 that is not taken as a portion through conduit 40 passes downstream by way of conduit 42.

In another embodiment of process 10, the $H_2/CO$ molar ratio of the feed to Fischer-Tropsch unit 24 is controlled by passing only a portion of the synthesis gas stream passing through conduit 16 to membrane system 18 by way of conduit 44. The remaining portion of the synthesis gas stream then passes by way of conduit 46 and is combined with the retentate stream passing to Fischer-Tropsch unit 24 through conduit 22. The amount of the remaining portion of synthesis gas stream that is combined with the retentate stream is adjusted or controlled in a manner so as to provide a feed to Fischer-Tropsch unit 24 having a desired the $H_2/CO$ molar ratio.

The following examples are provided to further illustrate the invention, but they should not be construed as limiting its scope.

Example 1 (Pure Palladium Membrane)

This Example 1 describes the preparation of a palladium-only hydrogen separation membrane system that was tested as presented in Example 3 for its performance in the separation of hydrogen from gas mixtures that also contain carbon monoxide and as a function of carbon monoxide concentration and time.

Initial Preparation of Tubular Porous Support

A 1 inch OD×15 inch length×0.1 inch wall thickness porous Hastelloy X inside-out pressed stainless steel tubular support was supplied by Mott Corporation. The tube was wrapped at the two ends with one layer of Teflon tape. One end of the tube was closed.

Two 500 ml-Erlenmeyer flasks, each containing 0.20-0.25 g of eggshell catalyst, 1 micron centered distribution, were mixed with 250 ml of DI water. The resulting slurry was then divided equally between 4 L of DI water in a 5 L glass beaker and 3.5 L of DI water in a 4 L glass beaker. The slurries were well mixed.

The porous tube assembly was connected to a vacuum pump with the vacuum adjusted to 25-30" Hg. The porous metal support assembly with the vacuum was immersed into slurry with slurry solution being added until there was no more reserve solution.

Following the application of the slurry, the vacuum was disconnected, and the Teflon tape and excess water inside the tube were removed.

The tubular support was then dried in an air circulating oven for at least 2 hours at 140° C. followed by reconnecting the tubular support to a vacuum of 25-30" Hg. While under the vacuum, the powder on the surface of the porous section was smoothed involving the removal of excess catalyst.

The above process was repeated using eggshell catalyst having a 0.5 micron centered distribution, with the exception that surface smoothing was omitted in the second deposition operation.

Plating Operation

The plating solution used to form the palladium membrane layer comprised 250 grams DI water, 198 ml of 28-30% ammonium hydroxide solution, 4.0 grams of tetraaminepalladium (II) chloride ($Pd(NH_3)_4Cl_2H_2O$), 40.1 grams ethylenediaminetetraacetic acid disodium salt ($Na_2EDTA_2H_2O$) and sufficient deionized water to make 1 L total volume to provide a solution with a Pd metal ion concentration of about 4 g/L. A peristaltic pump was utilized to circulate the solution about the support while applying vacuum to the support. Plating took place at a temperature of 50° C. for 5-10 minutes under 4-6 inches Hg vacuum and then continuously for 90 minutes. The bath was circulated at a rate of 1.4 L per minute. The membrane assembly was removed from the plating bath and washed with deionized water until the conductivity was less than 5 μS. The membrane was dried in an air circulating oven for at least 2 hours at 140° C. and cooled to 40° C.

Annealing Operation

The membrane assembly was annealed by increasing the temperature from 40° C. to 400° C. @2° C./min. in nitrogen. The gas mixture was transitioned 5 from 100% nitrogen to 100% hydrogen over the period of 1 hour and the heating continued to 520° C. The membrane assembly was held at this temperature overnight. The membrane assembly was then cooled to 400° C. and transitioned back to pure nitrogen and held for 2 hours before cooling to room temperature.

Polishing Operation

The membrane assembly was polished on a robotic polisher from Acme manufacturing with a SCOTCH BRITE® satin buff (UPC 00048011645339, 3M Corporation) under conditions set to provide desired polishing and surface properties of the polished surface. The SCOTCH BRITE rotary fibrous buff and method of its use are described in detail in U.S. Patent Application, Ser. No. 61/977,796, filed 10 Apr. 2014, entitled "A Method of Making a Supported Gas Separation Membrane." This disclosure is incorporated herein by reference upon its publication.

Repeating of Operations

The steps of plating, washing, drying, annealing and polishing operations were repeated until a leak-tight membrane system was achieved. This series of steps was repeated four times to provide a leak-tight, sealed membrane at 100 psi. The membrane had a hydrogen permeance of 40 $Nm^3/m^2/hr/bar$.

Example 2 (Gold-on-Palladium Membrane)

This Example 2 describes the preparation of a gold-on-palladium hydrogen separation membrane system that was tested as presented in Example 4 for its performance in the separation of hydrogen from gas mixtures that also contain carbon monoxide and as a function of carbon monoxide concentration and time.

Initial Preparation of Tubular Porous Support

The initial preparation of the 1 inch OD×15 inch length× 0.1 inch wall porous Hastelloy X stainless tubular support of this Example 2 was the same as that described in Example 1.

Palladium Plating Step

The palladium plating step in the preparation of the gold-on-palladium membrane of this Example 2 was the same as that described in Example 1.

Annealing Step

The annealing step in the preparation of the gold-on-palladium membrane of this Example 2 was the same as that described in Example 1.

Polishing Step

The membrane was polished on a robotic polisher from Acme manufacturing with a Trizact A3 belt from 3M under conditions set to provide desired polishing and surface properties of the polished surface. The Trizact belt and other related abrading media and method of their use are described in detail in U.S. Patent Application, Ser. No. 61/977,790, filed 10 Apr. 2014, entitled "A Method of Making a Supported Gas Separation Membrane." This disclosure is incorporated herein by reference upon its publication.

Repeating of Sets

The steps of palladium plating, washing, drying, annealing and polishing process was repeated until a leak-tight membrane was obtained. The series of steps was repeated four times to provide a leak-tight, sealed membrane at 100 psi. The membrane had a permeance of 41 $Nm^3/m^2/hr/bar$.

Gold Plating Step

The palladium plated membrane was abraded and placed in a gold plating bath containing of 1300 ml of 0.08% Chloroauric Acid. The bath temperature was maintained at 20° C. The membrane assembly was turned with overhead stirring motor at a rate of about 50 rpm. 1 ml of 30% hydrogen peroxide ($H_2O_2$) was delivered via pipette to the center of the gold plating bath. After two hours, 0.25 ml of 30% hydrogen peroxide was added in the same manner.

After the gold plating step was completed, the membrane was placed in a total volume (1300 ml) of DI water for an hour, thoroughly rinsed with DI water, and dried at 140° C. The gold plated membrane was transferred to a hydrogen annealing oven whereby it was annealed in an atmosphere of pure $H_2$ for 6 hours at a temperature of 550° C. Following the hydrogen annealing of the gold plated membrane, it was then washed, dried and polished as described in Example 1. The gold plating process was repeated until the resulting membrane contained 8% gold with a thickness of 7.8 microns.

Example 3 (Test of Palladium-Only Membrane of Example 1)

This Example 3 presents performance data for the palladium-only hydrogen separation membrane of Example 1 in the separation of hydrogen from gas mixtures that contain various concentrations of carbon monoxide. The performance of the palladium-only hydrogen separation membrane is presented as a function of carbon monoxide concentration.

The following Table 1 presents the composition of the various feed streams processed by the palladium-only hydrogen separation membrane in its testing. The palladium-only hydrogen separation membrane was tested under the conditions of 15 bar and 450° C.

TABLE 1

Feed stream compositions used in the performance testing of palladium-only membrane

| Feed Component | SLPH (0 vol % CO) | SLPH (2.5 vol. % CO) | SLPH (5.0 vol. % CO) | SLPH (7.5 vol. % CO) | SLPH (10.0 vol. % CO) |
|---|---|---|---|---|---|
| $H_2$ | 472.6 | 472.6 | 472.6 | 472.6 | 472.6 |
| $N_2$ | 413.8 | 425.2 | 394.1 | 363.3 | 343.6 |
| $CH_4$ | 42.6 | 42.6 | 42.6 | 42.6 | 42.6 |
| CO | 0 | 29.8 | 61.6 | 92.4 | 123.2 |
| $H_2O$ | 261.5 | 261.5 | 261.5 | 261.5 | 261.5 |
| total | 1190.5 | 132.1 | 1235.8 | 1234.5 | 1243.5 |

*SLPH = standard liters per hour

Table 2 presents the composition of the permeate as a function of time and carbon monoxide concentration in the feed gas mixture.

FIG. 1 presents the same data to further illustrate the phenomenon of rapid decline of membrane performance when the carbon monoxide concentration approaches 10 volume percent. The data demonstrate low resistance of the palladium-only membrane to the deleterious effect of carbon monoxide and the impact of carbon monoxide concentration in the feed gas mixture on the performance of the palladium-only membrane selectivity.

TABLE 2

Carbon monoxide concentration in feed gas mixture and permeate composition as a function of time

| Time (hrs) | Mole % CO in Feed | $H_2$ in Permeate (mole %) | $N_2$ in Permeate (mole %) | $CH_4$ in Permeate (mole %) | CO in Permeate (mole %) |
|---|---|---|---|---|---|
| 627 | 2.5 | 100 | 0 | 0 | 0 |
| 669 | 2.5 | 100 | 0 | 0 | 0 |
| 693 | 2.5 | 99.9 | 0.1 | 0 | 0 |
| 717 | 5.0 | 99.9 | 0.1 | 0 | 0 |
| 771 | 5.0 | 100 | 0 | 0 | 0 |
| 790 | 5.0 | 100 | 0 | 0 | 0 |
| 836 | 5.0 | 99.9 | 0.1 | 0 | 0 |
| 861 | 5.0 | 99.9 | 0.1 | 0 | 0 |
| 870 | 5.0 | 98.8 | 1.1 | 0.6 | 0.05 |
| 895 | 5.0 | 98.8 | 1.1 | 0.6 | 0.05 |
| 936 | 7.5 | 99.9 | 0.1 | 0 | 0.0 |
| 958 | 7.5 | 99.8 | 0.1 | 0.01 | 0.02 |
| 981 | 7.5 | 99.8 | 0.1 | 0.01 | 0.02 |
| 1007 | 7.5 | 100 | 0 | 0 | 0 |
| 1011 | 7.5 | 99.2 | 0.67 | 0.06 | 0.05 |
| 1029 | 7.5 | 98.8 | 1.1 | 0.09 | 0.04 |
| 1054 | 7.5 | 98.8 | 1.12 | 0.11 | 0.04 |
| 1125 | 7.5 | 98.9 | 0.85 | 0.17 | 0.08 |
| 1157 | 10.0 | 98.9 | 0.85 | 0.17 | 0.08 |
| 1174 | 10.0 | 98.9 | 0.85 | 0.17 | 0.08 |
| 1199 | 10.0 | 96.7 | 2.34 | 0.42 | 0.5 |
| 1225 | 10.0 | 96.7 | 2.37 | 0.42 | 0.5 |
| 1255 | 10.0 | 85.8 | 9.96 | 1.15 | 2.91 |

Example 4 (Test of Gold-on-Palladium Membrane of Example 2)

This Example 4 presents performance data for the gold-on-palladium hydrogen separation membrane of Example 2 in the separation of hydrogen from gas mixtures that contain various concentrations of carbon monoxide. The performance of the gold-on-palladium hydrogen separation membrane is presented as a function of carbon monoxide concentration and time.

The following Table 3 presents the composition of the various feed streams processed by the gold-on-palladium hydrogen separation membrane in its testing. The gold-on-palladium hydrogen separation membrane was tested under the conditions of 15 bar and 450° C.

TABLE 3

Feed stream compositions used in the performance testing of gold-on-palladium membrane

| Feed Component | SLPH* CO conc. (5%) | SLPH CO conc. (10.1%) | SLPH CO conc. (12.6%) | SLPH CO conc. (15%) | SLPH CO conc. (15%) | SLPH CO conc. (18.2%) | SLPH CO conc. (20%) | SLPH CO conc. (22.5%) |
|---|---|---|---|---|---|---|---|---|
| $H_2$ | 548.3 | 548.3 | 548.3 | 548.3 | 548.3 | 548.3 | 548.3 | 548.3 |
| $N_2$ | 322.5 | 260 | 229.8 | 111.9 | 199.6 | 120.9 | 120.9 | 70.6 |
| $CH_4$ | 41.6 | 41.6 | 41.6 | 41.6 | 41.6 | 41.6 | 41.6 | 41.6 |
| CO | 62.2 | 124.3 | 155.4 | 185.5 | 185.5 | 225.6 | 247 | 275 |
| $H_2O$ | 261 | 261 | 261 | 348 | 261 | 300 | 300 | 300 |
| total | 1236.1 | 1235.8 | 1236.6 | 1235.9 | 1236.4 | 1236.5 | 1236.4 | 1236.5 |
| $H_2$/CO | 8.8 | 4.4 | 3.5 | 2.9 | 2.9 | 2.4 | 2.2 | 2.0 |

*SLPH = standard liters per hour

Table 4 presents the composition of the permeate as a function of time and carbon monoxide concentration in the feed gas mixture.

Figure 2:
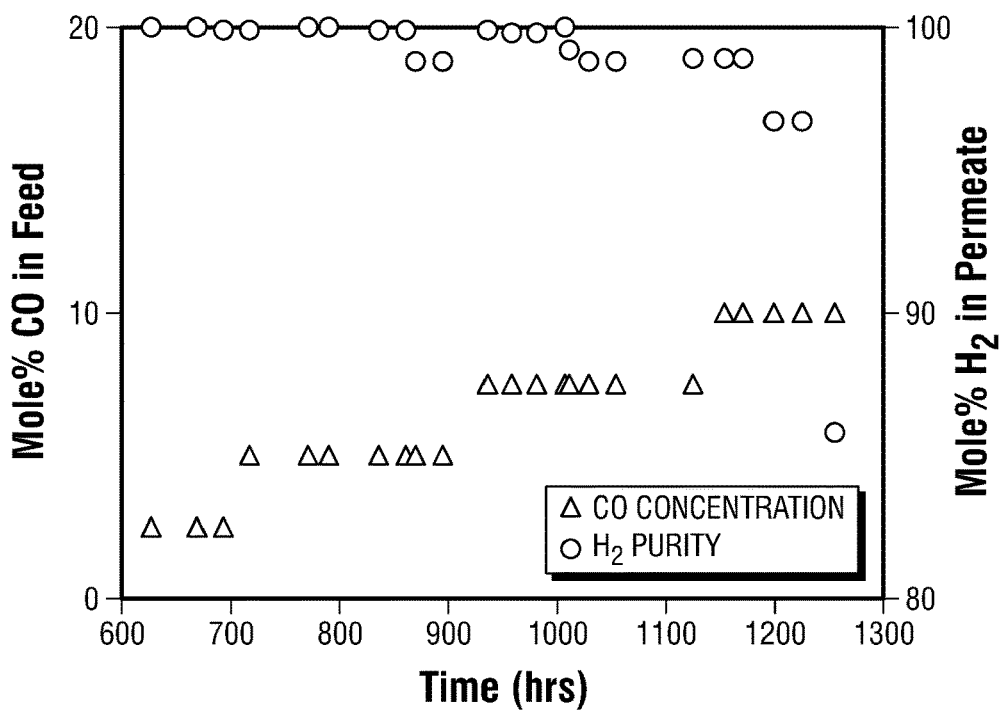
FIG. 2 presents a chart of the performance of the palladium-only membrane used for separating hydrogen from hydrogen gas mixtures containing various concentrations of carbon monoxide. The chart shows the hydrogen concentration of the permeate as compared to the carbon monoxide concentration in the membrane feed versus the time that the particular membrane feed was charged to the palladium-only membrane.
Figure 3:
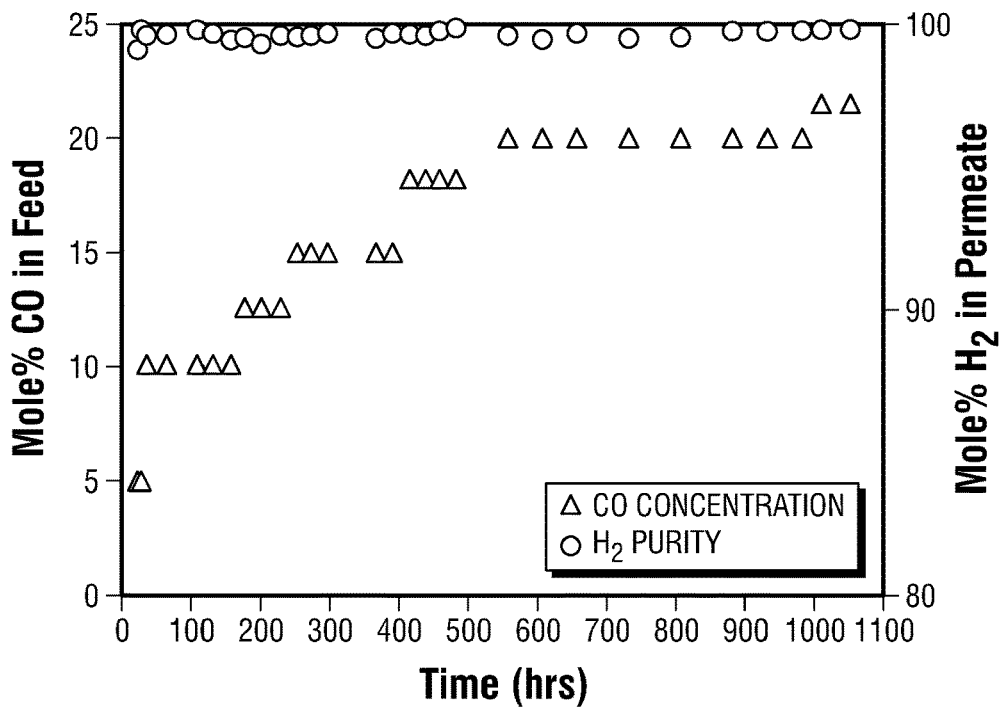
FIG. 3 presents a chart of the performance of the gold-on-palladium membrane used for separating hydrogen from hydrogen gas mixtures containing various concentrations of carbon monoxide. The chart shows the hydrogen concentration of the permeate as compared to the carbon monoxide concentration in the membrane feed versus the time that the particular membrane feed was charged to the gold-on-palladium membrane.

FIG. 3 presents the same data as is presented in Table 4 to further illustrate that the high concentration of carbon monoxide concentration in the feed gas mixture has little effect on the membrane performance for hydrogen separation. The data show that the gold-on-palladium membrane is resistant to negative effects of carbon monoxide on its performance in the separation of hydrogen. As may be observed from FIG. 2 the high hydrogen purity of the permeate is maintained even at the very high concentrations of carbon monoxide in the feed gas mixtures.

TABLE 4

Carbon monoxide concentration in feed gas mixture and permeate composition as a function of time

| Time (hrs) | Mole % CO in Feed | $H_2$ in Permeate (mole %) | $N_2$ in Permeate (mole %) | $CH_4$ in Permeate (mole %) | CO in Permeate (mole %) |
|---|---|---|---|---|---|
| 23 | 5 | 99.11 | 0.71 | 0.18 | 0.01 |
| 28 | 5 | 99.80 | 0.11 | 0.01 | 0.01 |
| 36 | 10.1 | 99.63 | 0.34 | 0.03 | 0.01 |
| 65 | 10.1 | 99.66 | 0.31 | 0.02 | 0.01 |
| 109 | 10.1 | 99.81 | 0.16 | 0.02 | 0.01 |
| 131 | 10.1 | 99.67 | 0.31 | 0.02 | 0.01 |
| 157 | 10.1 | 99.48 | 0.49 | 0.02 | 0.01 |
| 177 | 12.6 | 99.52 | 0.45 | 0.02 | 0.01 |
| 201 | 12.6 | 99.31 | 0.67 | 0.02 | 0.00 |
| 229 | 12.6 | 99.69 | 0.28 | 0.02 | 0.01 |
| 253 | 15 | 99.47 | 0.49 | 0.03 | 0.01 |
| 273 | 15 | 99.59 | 0.37 | 0.03 | 0.01 |
| 297 | 15 | 99.76 | 0.20 | 0.03 | 0.01 |
| 367 | 15 | 99.49 | 0.47 | 0.02 | 0.01 |
| 391 | 15 | 99.70 | 0.24 | 0.04 | 0.02 |
| 416 | 18.2 | 99.66 | 0.28 | 0.04 | 0.02 |
| 439 | 18.2 | 99.61 | 0.33 | 0.04 | 0.02 |
| 459 | 18.2 | 99.73 | 0.21 | 0.05 | 0.01 |
| 483 | 18.2 | 99.86 | 0.08 | 0.05 | 0.02 |
| 557 | 20 | 99.60 | 0.33 | 0.05 | 0.02 |
| 607 | 20 | 99.47 | 0.46 | 0.05 | 0.02 |
| 657 | 20 | 99.71 | 0.22 | 0.06 | 0.02 |
| 732 | 20 | 99.50 | 0.41 | 0.06 | 0.03 |
| 807 | 20 | 99.53 | 0.38 | 0.05 | 0.04 |
| 882 | 20 | 99.76 | 0.17 | 0.05 | 0.02 |
| 932 | 20 | 99.75 | 0.17 | 0.04 | 0.03 |
| 982 | 20 | 99.71 | 0.22 | 0.05 | 0.02 |
| 1010 | 22.5 | 99.81 | 0.12 | 0.05 | 0.02 |
| 1052 | 22.5 | 99.83 | 0.08 | 0.06 | 0.03 |

That which is claimed is:

1. A process for converting gaseous hydrocarbons to higher molecular weight hydrocarbons, wherein said process comprises:
   providing a carbon monoxide resistant gold-on-palladium supported gas separation membrane system, comprising a porous support having deposited thereon a gold-on-palladium membrane, comprising a gold layer on a palladium layer and that is operatively connected between a steam reforming unit and a Fischer-Tropsch unit;
   passing at least a portion of a synthesis gas stream yielded from said steam reforming unit and having a synthesis gas stream hydrogen-to-carbon monoxide molar ratio in the range of from 1:1 to 10:1 as a membrane system feed to said carbon monoxide resistant gold-on-palladium supported gas separation membrane system;
   yielding from carbon monoxide resistant gold-on-palladium supported gas separation membrane system a permeate stream, comprising hydrogen, and a retentate stream, having a retentate stream hydrogen-to-carbon monoxide ratio;
   passing said retentate stream as a Fischer-Tropsch unit feed to said Fischer-Tropsch unit; and
   yielding from said Fischer-Tropsch unit a Fischer-Tropsch synthesis product.

2. The process as recited in claim 1, further comprising:
   combining a remaining portion of said synthesis gas stream with said retentate stream in an amount so as to provide said Fischer-Tropsch unit feed having a desired hydrogen-to-carbon monoxide molar ratio.

3. The process as recited in claim 1, further comprising:
   combining a portion of said permeate stream with said retentate stream in an amount so as to provide said Fischer-Tropsch unit feed having a desired hydrogen-to-carbon monoxide molar ratio.

4. The process as recited in claim 1, further comprising:
   controlling a pressure differential across said gold-on-palladium membrane so as to provide said retentate stream having a desired retentate stream hydrogen-to-carbon monoxide molar ratio.

5. The process as recited in claim 4, wherein said synthesis gas stream comprises hydrogen at a concentration in the range of from 30 to 70 vol. % and having a hydrogen-to-carbon monoxide molar ratio is in the range of from 1.5:1 to 10:1, and wherein said permeate stream comprises from 1 vol. % to 20 vol. % of the hydrogen contained in said at least a portion of said synthesis gas stream.

6. The process as recited in claim 5, wherein said retentate stream hydrogen-to-carbon monoxide molar ratio is less than said synthesis gas stream hydrogen-to-carbon monoxide molar ratio and is in the range of from 1.4:1 to 2.3:1.

7. The process as recited in claim 6, wherein said desired retentate stream hydrogen-to-carbon monoxide molar ratio is in the range of from 1.5:1 to 2.2:1.

8. The process as recited in claim 2, wherein said synthesis gas stream comprises hydrogen at a concentration in the range of from 30 to 70 vol. % and having a hydrogen-to-carbon monoxide molar ratio is in the range of from 1.5:1 to 10:1, and wherein said permeate stream comprises from 1 vol. % to 20 vol. % of the hydrogen contained in said at least a portion of said synthesis gas stream.

9. The process as recited in claim 8, wherein said desired hydrogen-to-carbon monoxide molar ratio is in the range of from 1.5:1 to 2.2:1.

10. The process A process as recited in claim 3, wherein said synthesis gas stream comprises hydrogen at a concentration in the range of from 30 to 70 vol. % and having a hydrogen-to-carbon monoxide molar ratio is in the range of from 1.5:1 to 10:1, and wherein said permeate stream comprises from 1 vol. % to 20 vol. % of the hydrogen contained in said at least a portion of said synthesis gas stream.

11. The process as recited in claim 10, wherein said desired hydrogen-to-carbon monoxide molar ratio is in the range of from 1.5:1 to 2.2:1.

12. The process as recited in claim 11, further comprising:
passing said Fischer-Tropsch product to a separation system for separating said Fischer-Tropsch product into hydrocarbon fractions.

* * * * *